United States Patent [19]

Forren

[11] Patent Number: 5,279,574

[45] Date of Patent: Jan. 18, 1994

[54] CATHETER AND ASSOCIATED INTRAVENOUS TUBING PROTECTIVE ASSEMBLY

[76] Inventor: Gary L. Forren, 800 Edenwood Cir., Louisville, Ky. 40243

[21] Appl. No.: 917,776

[22] Filed: Jul. 21, 1992

[51] Int. Cl.$^5$ ............................................. A61M 5/00
[52] U.S. Cl. ................................. 604/174; 128/879; 604/179
[58] Field of Search .................. 604/174, 179, 180; 128/877, 878, 879

[56] References Cited

U.S. PATENT DOCUMENTS

| 824,174 | 6/1906 | Clark et al. | 128/879 |
|---|---|---|---|
| 973,330 | 10/1910 | Wood | 128/879 |
| 2,043,153 | 6/1936 | Cox | 128/879 |
| 2,139,897 | 12/1938 | Kessler | 128/879 |
| 3,074,399 | 1/1963 | Bitting | 128/879 |
| 3,182,657 | 5/1965 | Zurbuchen | 128/879 |
| 3,189,073 | 6/1965 | Todd | 128/878 |
| 3,415,244 | 12/1968 | Block | 128/879 |
| 3,722,508 | 3/1973 | Roberts | 604/174 |
| 4,615,339 | 10/1986 | Siwek | 128/878 |
| 4,669,458 | 6/1987 | Abraham et al. | 604/180 |
| 4,793,486 | 12/1988 | Konopka et al. | 604/174 |
| 4,919,150 | 4/1990 | Grant | 128/877 |
| 5,016,648 | 5/1991 | Brown et al. | 128/879 |
| 5,190,530 | 3/1993 | Greef et al. | 604/179 |

Primary Examiner—Paul J. Hirsch
Attorney, Agent, or Firm—Camoriano & Smith

[57] ABSTRACT

A protective assembly for the arm and leg of a patient to prevent movement and/or displacement of a catheter and the intravenous tubing attached to said catheter by casual movement of the patient within the environment of a hospital room or the home or the like. The assembly comprises a bifurcated assembly defining a mouth communication with a cavity for encompassing a limb of a patient. The two halves of the assembly are hinged together and, when closed defining an opening communicating with the cavity to receive the intravenous tubing leading to a catheter implanted in the arm of the patient. A pair of clips positioned adjacent the opening serve to immobilize the part of the tubing from the clips to catheter when the patient moves the arm.

17 Claims, 2 Drawing Sheets

CATHETER AND ASSOCIATED INTRAVENOUS TUBING PROTECTIVE ASSEMBLY

BACKGROUND OF THE INVENTION

This invention relates to an assembly for the protection of individuals against the displacement of implanted catheters due to movement of the associated limb and, more particularly, to an assembly which immobilizes the tubing leading from an implanted catheter against movement of the limb into which the catheter is implanted.

When an individual, whether in a hospital or under home care, is required to have intravenous feeding, even casual movement of the arm or limb into which the catheter is positioned can cause discomfort when the catheter or the bandages are displaced due to the movement of the attached intravenous tubes and catheter. Such movement not only occurs when sleeping, but in working hours when the patient momentarily forgets. This situation is exacerbated in situation involving children and geriatric patients. Typical hospital practice calls for bandages to be wrapped around the catheter and the end of the tubing attached to the catheter to prevent displacement. This is entirely unsatisfactory since the leverage of the tubing extending some distance from the fluid reservoir is often sufficient to cause the catheter to be displaced or removed from its position entirely. This can be a dangerous situation in certain instances. Thus it is extremely desirable to provide some device which can minimize the anxiety and discomfort of patients caused by even the most casual and normally expected movements.

SUMMARY OF THE PRESENT INVENTION

A protective assembly to be worn by a patient on a limb being fed by intravenous tubing and a catheter comprises a bifurcated body having hingedly connected first and second halves which complimentary fit together when the bifurcated body is closed. The body further defines in the closed position an angularly shaped collar bifurcated into first and second portions which are integrally connected to a bifurcated wall that further diverges into a bifurcated central housing. The central housing defines a central cavity for receiving and encompassing the limb of a patient and intravenous tubing leading to a catheter penetrating the limb. The central housing further defines in the closed position at least one opening communicating with the cavity for receiving the intravenous tubing. A securing device is attached to the housing adjacent the opening for immobilizing the intravenous tubing against displacement between the opening and the point of connection of the tubing with the catheter. The housing is also provided with a securing device for releasable securing the body in a closed position.

DETAILED DESCRIPTION OF THE PREFERRED EMBODIMENT

Figure 1:
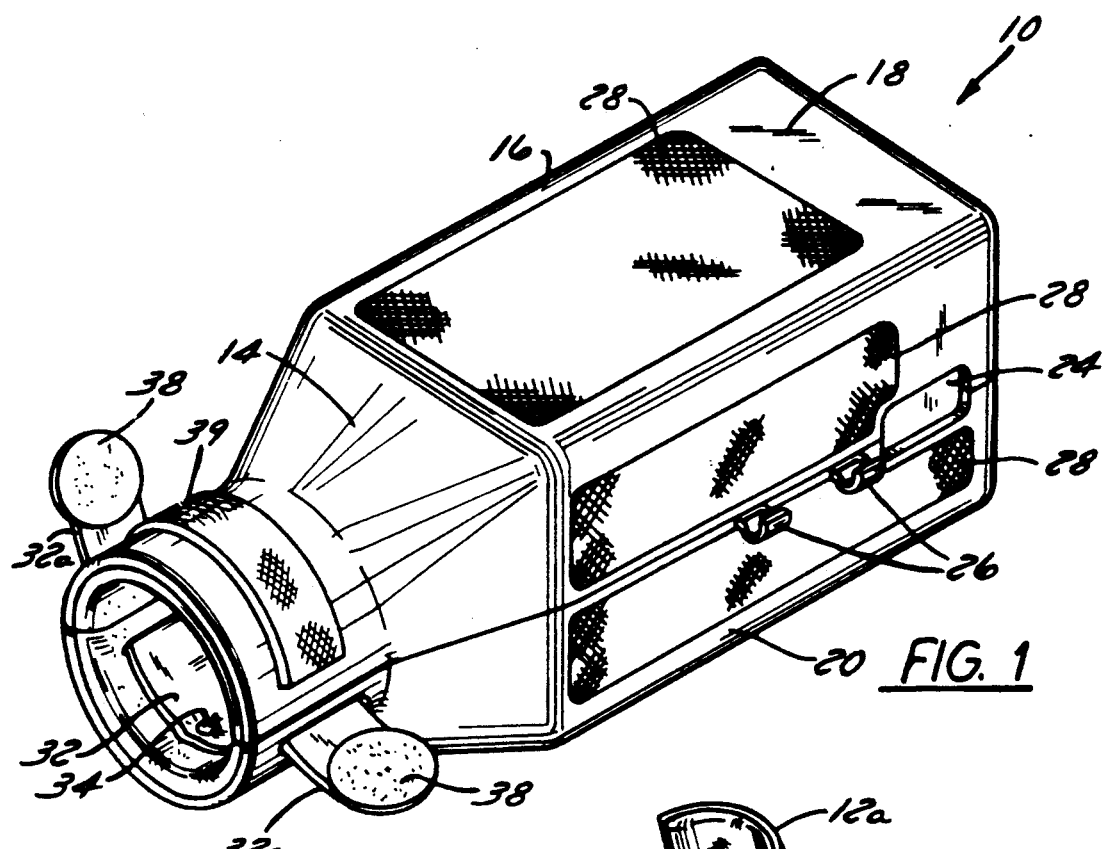
FIG. 1 is a perspective view of a protective assembly of the present invention when in the closed position.
Figure 2:
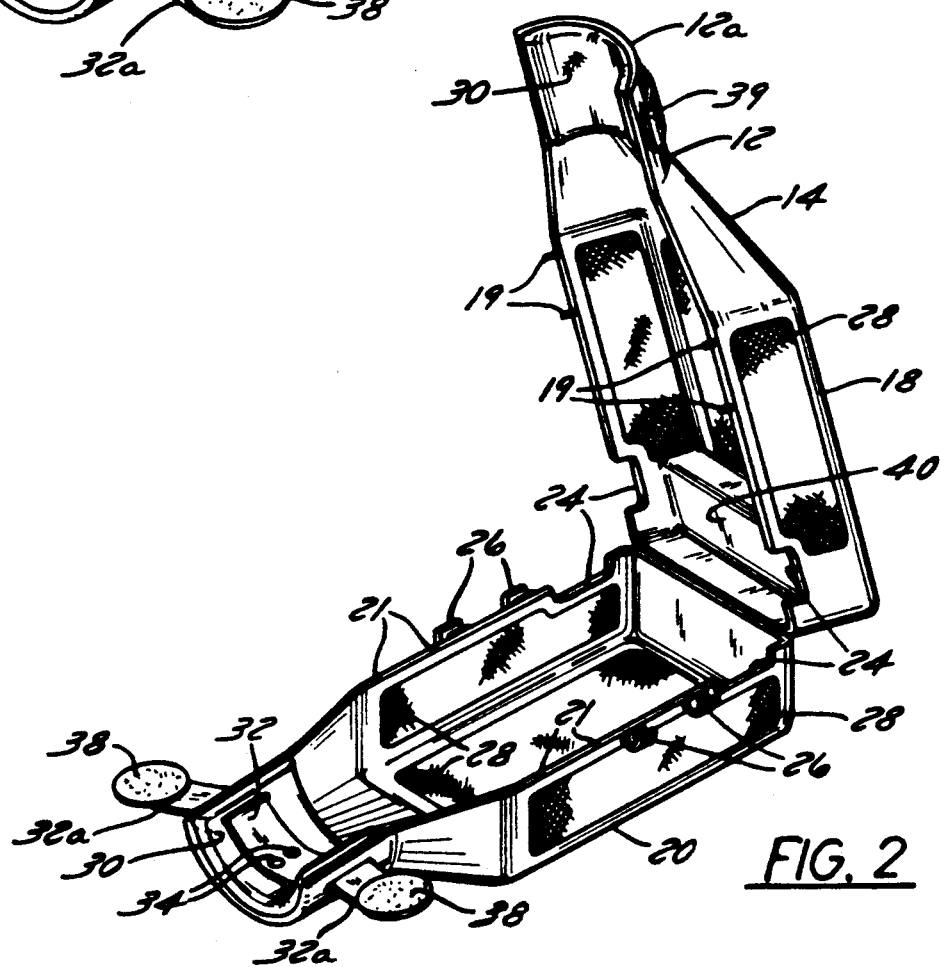
FIG. 2 is a perspective view of the present invention when in the open position.
Figure 6:
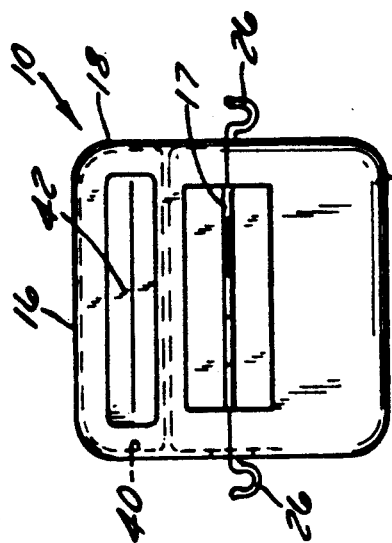
FIG. 6 is a view of the end opposite the mouth end, i.e, the bottom end, illustrating the hinge mechanism for the assembly and the opening into the bag storage compartment.
Figure 4:
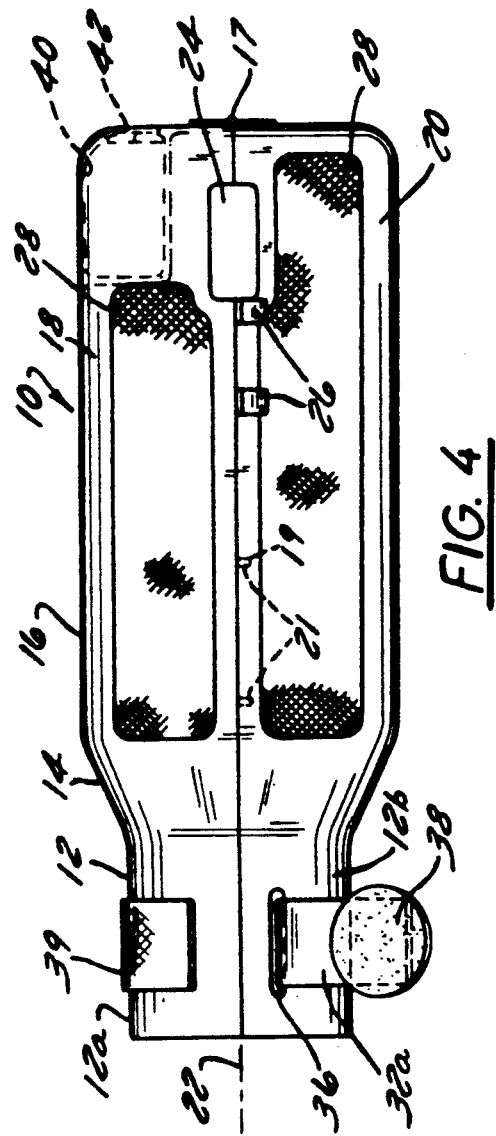
FIG. 4 is a side view of the present invention.

Referring first to the perspective views of FIGS. 1 and 2, the intravenous feeding protective assembly 10 constructed in accordance with the present invention comprises generally an cylindrical shaped collar member 12, a transition wall 14 which diverges away from the collar member 12 to a central housing 16. As is clearly demonstrated by FIG. 2, the assembly 10 is bifurcated into two complimentary halves 18 and 20 generally along the line 22. The halves 18 and 20 are preferably hinged together by a hinge element 17 (seen in FIGS. 3, 4 & 6) at the end away from collar member 12, i.e., the bottom of the assembly 12, although, as discussed hereinafter, in some situations it may be desirable to place the hinge element 17 along the side of assembly 10. To provide adequate registry of the two halves, one half may be provided a plurality of pins or tabs 19 and the other complimentary openings 21.

The central housing 16, when the assembly 10 is in a closed position, defines a central cavity which communicates with the mouth opening defined by the collar 12. Additionally central housing 16 is provided with a pair of openings 24, perhaps best illustrated together by FIG. 2. The openings 24, which are defined by the cutouts in each half 18 and 20, are located toward the bottom of the assembly 12 to facilitate the entry of the intravenous tubing into the cavity leading to the catheter positioned in the patient's arm. Mounted to one of the halves of the central housing and adjacent openings 24 are preferably at least two tube clips 26 adapted to receive and secure the intravenous tubing. The clips are preferably of the pressure type such that gentle manual movement of the tube will cause the clip prongs to flex outwardly and allow the tube to be inserted within the clip prongs. Any securing member that serves to secure the tubing against movement between the point of securement and the catheter without cutting off circulation of the intravenous fluid would be suitable, however. It is important that the clips 26 be placed slightly forward of the openings 24, i.e., toward the collar 12, to facilitate the stability of the intravenous tubing. The catheter will ordinarily be placed in the patient's arm such that, when the assembly 10 is closed, the catheter and the clips 26 will be adjacent each other. This means that the intravenous tubing will be held in place by the clips 26, enter opening 24 and double back to the catheter. The positioning of the openings 24 toward the rear of the assembly and the clips 26 forward of the openings 24 minimizes any displacement of the tubing that would otherwise occur due to normal patient movement. It is preferred that clips 26 secure the tubes by a friction or press fit without causing any change in the internal volume of the intravenous tubes.

The central housing 16 is illustrated as having a parallelpiped configuration. Such a configuration allows the housing to be positioned flat on a table or the like while the patient positions an arm in the half against the table and the catheter is inserted in the arm. The shape helps to minimize movement during insertion. However, the exact configuration is primarily a function of the intended purpose and the circumstances of the intended use. Other housing configurations such as cylindrical, for example, may be more suitable in some circumstances. Additionally, the separate halves need not be identical or mirror images in order to accommodate other limb shapes such as, for example, a foot.

It is additionally desirable that the interior of the assembly 10 be open to the proper circulation of air when being used. Accordingly the central housing 16 may be provided with multiplicity of openings. As shown in the various views of assembly 10, portions of the four walls of central housing 16 are comprised of an open mesh 28 which, only allows the circulation of air within, but permits visual observation of the status of the catheter, connected intravenous tubing, and patient's limb.

Figure 3:
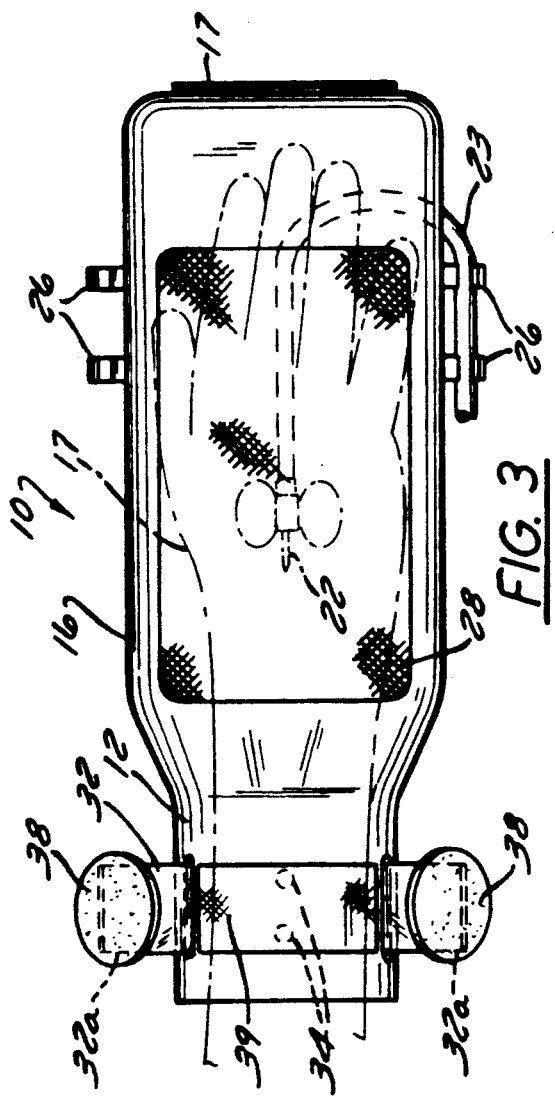
FIG. 3 is a view from the top of the present invention illustrating the connection of the flexible fastening strap connected to the collar of the assembly.

As depicted in phantom in FIG. 3, a patient's hand and forearm 17 are positioned with a catheter 22 used to mounted on the forearm. Tubes 23 lead away from catheter 22 and is secured by fasteners 26 as discussed above.

The criteria for selection of the proper material used in the manufacturing of the protective assembly of the present invention depends primarily on the strength required, minimal weight desired and compatibility with proper medical regulations with respect to materials. It has been found that plastic material such as medical grade polyethylene or polypropylene amenable to formation of the assembly through injection or rotary molding processes is suitable. The mesh areas 28 can also be formed through a molding process as desired. Thicknesses can vary depending upon the desired use, but applicant has found that polyethylene having a thickness of between about 100 to 400 mill is suitable. Because collar 12 may be used to support a fastening assembly that serves to secure assembly 10 in the closed position (as discussed below), it is desirable that the thickness be greater than the other portions of the assembly. For example, a thickness of about 300 to 400 mills may be suitable. The entire internal surface of collar 12 may be lined and padded with a soft material 30 such as terry cloth to provide further comfort to the patient.

Figure 5:
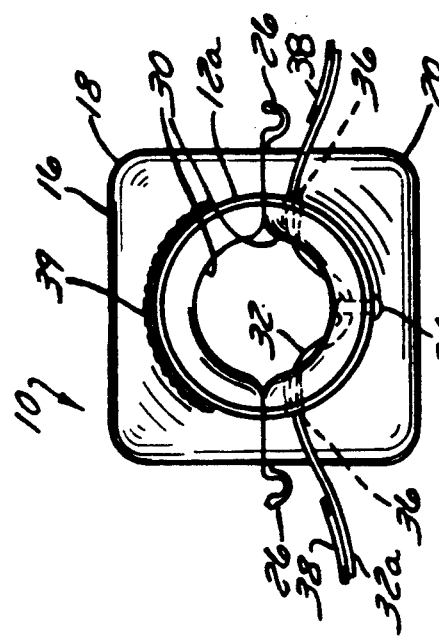
FIG. 5 is a view of the mouth end of the invention.

A strap 32 of flexible and elastic material of a length less than about one-half the circumference is secured at its midpoint to the interior surface of one of the portions of collar 12 by a pair of rivets 34 seen in FIGS. 1 and 3. Preferably the strap 32 is attached to the half of the collar 12 upon which the patient rests his or her limb. The precise means by which the strap 32 is secured, however, is not critical. The strap 32 then is threaded through a pair of slots 36 defined in portion 12 and through openings in the terry cloth lining in registry with the slots. Each distal end 32a of the strap 32 has a circular shape which is preferably slightly larger in diameter than the length of slots 36, thereby preventing unintentional dethreading of the distal end 32a there through. Each distal end 32a is provided with a pad 38 of preferably a velcro-type fastener material. A strip 39 of compatible velcro-type fastener material is attached to the outer surface of collar 12 on portion 12a. Although it is contemplated that the assembly 10 will be made in different sizes to accommodate adults and children and the variations in limb diameter, some accommodation within sizes is desired. As best seen in FIG. 5, once an individual's limb rests against soft material 30 (and strap 32 inside collar 12) the assembly 10 is closed, depending upon the diameter of the limb within collar 12, the limb may press against the strap 32 causing it to flex slightly outward. It is thus desirable that the strap 32 be adjustable to prevent an undue increase in the tension that would otherwise be built up against the patient's arm as the strap 32 is fastened at its distal ends. Strap 32, being elastic, can be stretched as desired and fastens to strip 39.

When, for example, a patient is being washed, it is desirable to protect the assembly 10 and the limb of the patient from contact with the water. Assembly 10 therefore may be provided with an optional compartment 40 (seen in FIG. 2 and in phantom in FIG. 6) to store waterproof bags having a single drawstring to facilitate manipulation by the patent to encompass the assembly 10 which bags can be tied as desired about assembly 10 and the protruding limb. The compartment 40 located at the bottom end of assembly 10 may be provided with a leaf spring cloth covered door 42 which is normally biased shut but can easily be pried open by an individual's fingers to retrieve the bag stored therein. While the bags may be fastened, to the assembly, it is preferable that the bags be entirely separate as prudent medical practice dictates sterilization or discard after use.

Thus, when being used it may be seen that the assembly 10 may be opened and laid upon a utility table. The patient then places a limb within the assembly and rests the same on the lining of collar 12 while the catheter and the intravenous tube is being positioned in place. The tube is then carefully placed in one of the half openings in the lower half 20 of the central housing 16 and the assembly is closed. The tube is then pressed into the pair of clips 26 adjacent the opening 4 and the fastening strap 32 wrapped around portion 12a of collar 12 and secured by pad 38 to strips 39 with a tension comfortable to the patient. The patient then is free to move within the local environment without concern that the catheter may be jostled or displaced from position.

Other configurations of the assembly 10 may become apparent from a reading of the description herein. For example, the assembly 10 may be provided with a hinge mechanism on one side and the bottom provided with an opening to permit the patient's limb to extend completely through and out the bottom end of the assembly 10. This, for example, would give the patient the ability to use the hand and fingers of the arm bearing the catheter if considered prudent by the medical advisors. Therefore, the following claims are meant to cover the variations and those design changes which are fall within the spirit thereof.

I claim:

1. A catheter immobilizing and protective assembly in combination with tubing and a catheter connected to a limb of a patient being fed intravenously, said assembly comprising a bifurcated body having a first and second half hingedly connected to each other, said first and second halves adapted to be positioned in an open position and closed position, said body defining in the closed position a mouth communicating with a central cavity sufficiently large wherein the inner surface of said body is spaced from the point of penetration of the catheter with the limb, said cavity being adapted to receive and encompass the limb of a patient and intravenous tubing leading to a catheter penetrating the limb, said halves collectively defining in the closed position at least one slot communicating with said cavity and located at one end thereof for receiving the intravenous tubing, tubing immobilizing fastener attached to said body adjacent said slot for immobilizing said intravenous tubing against displacement between said opening and the point of connection with said catheter;

transparent region in said body above said point of connection to permit viewing of the catheter and tubing; and means for releasably securing said body in the closed position.

2. The protective assembly of claim 1 in which said mouth is in the shape of an annular collar bifurcated into two collar halves adapted to fit snugly against the limb of a patient when said body is in the closed position, said releasable securing means being a predetermined length of flexible material threaded through a pair of spaced slots in one collar half and extending along the interior surface of said one collar half and circumscribing at least a portion of the outer surface of said other collar half when said body is in the closed position, said flexible material provided with adjustable fastening means at the distal ends thereof for securing the distal ends against movement relative to said other collar half when said body is in the closed position.

3. The protective assembly of claim 2 in which said adjustable fastening means further is for varying the tension of the flexible material about the limb of a patient within the mouth of said body when in the closed position.

4. The protective assembly of claim 3 in which the securing means is a flexible and elastic strap and said securing means is a fastener mounted on the distal end of said strap and a complimentary fastener mounted on said other element.

5. The protective assembly of claim 1 in which said halves are hinged together at the end away from said mouth.

6. The protective assembly of claim 1 including a storage compartment for storing a waterproof bag.

7. The assembly of claim 6 in which said storage compartment is mounted at the end of said assembly away from said mouth and defines a closable opening in said end.

8. The assembly of claim 1 in which said mouth is in the shape of an annular collar bifurcated into two collar halves adapted to fit snugly against the limb of a patient when said body is in the closed position, said collar being integrally connected to a bifurcated wall portion diverging into a bifurcated central housing portion defining said cavity, said central housing having the shape of a parallelpiped when in the closed position.

9. The assembly of claim 8 in which said central housing has walls provided with a multiplicity of apertures for permitting air circulation into said cavity.

10. The assembly of claim 9 in which said central body has wall portions provided with a mesh permitting viewing of the interior of said central housing.

11. The assembly of claim 1 in which said body has at least one flat side adapted to be positioned against a support surface when said catheter is connected to a limb.

12. A catheter immobilizing and a protective assembly in combination with intravenous tubing and a catheter connected to a limb of a patient being fed intravenously, said assembly comprising a body having a first and second halves adapted to being positioned in an open position and closed position in which said halves complimentary fit together and form a bifurcated central housing with a central cavity therein, said body further defining in the closed position an annularly shaped collar bifurcated into first and second portions integrally connected to a bifurcated wall diverging into said bifurcated central housing, said central cavity adapted to receive and encompass the extremity of a limb of a patient and the portion of the limb in which the catheter is inserted and to encompass the intravenous tubing leading to the catheter penetrating the limb, said halves collectively defining in the closed position at least one opening communicating with said cavity for receiving the intravenous tubing, said central housing having at least one flat side adapted to be supported by a support surface when the catheter is being penetrated into the limb of a patient, at least on tube immobilizing means attached to said central housing adjacent said opening for immobilizing the intravenous tubing against displacement between said opening and the point of connection of said tubing with the catheter;

transparent region in said body above the point of insertion to permit viewing of the catheter; and means for releasably securing said body in the closed position.

13. The assembly of claim 12 in which said releasable securing means is a predetermined length of flexible material fastened to the interior surface of said first portion of said collar, said first portion having a pair of slots displaced a predetermined distance from the position of fastening of said flexible material to said first portion, said flexible material threaded through said slots and adapted to circumscribe a portion of the outer surface of said second portion when said body is in the closed position, said flexible material provided with adjustable fastening means at the distal ends thereof for fastening the distal ends together when said body is in the closed position.

14. The assembly of claim 13 in which said central housing has the shape of a parallelpiped.

15. The assembly of claim 14 in which said central housing has walls provided with a multiplicity of apertures for permitting air circulation into said cavity.

16. The assembly of claim 15 in which said central body has wall portions provided with a mesh permitting viewing of the interior of said central housing.

17. The assembly of claim 13 in which said central housing defines two openings spaced on opposite sides of said body and said tube immobilizing means comprises a pair of tube fasteners each attached to said housing at a point intermediate an associated one of said openings and said collar.

* * * * *